US010493240B2

(12) United States Patent
Dillon et al.

(10) Patent No.: US 10,493,240 B2
(45) Date of Patent: Dec. 3, 2019

(54) STEERABLE CATHETER HANDLE

(71) Applicant: Cook Medical Technologies LLC, Bloomington, IN (US)

(72) Inventors: Travis E. Dillon, Winston-Salem, NC (US); Luke T. Jungles, Winston-Salem, NC (US); Michael Lee Williams, Pinnacle, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 190 days.

(21) Appl. No.: 15/655,066

(22) Filed: Jul. 20, 2017

(65) Prior Publication Data
US 2018/0028783 A1 Feb. 1, 2018

Related U.S. Application Data

(60) Provisional application No. 62/367,910, filed on Jul. 28, 2016, provisional application No. 62/367,918, (Continued)

(51) Int. Cl.
*A61M 25/01* (2006.01)
*A61M 25/09* (2006.01)
(Continued)

(52) U.S. Cl.
CPC .... *A61M 25/0147* (2013.01); *A61M 25/0026* (2013.01); *A61M 25/0041* (2013.01);
(Continued)

(58) Field of Classification Search
CPC ............ A61M 2025/015; A61M 25/01; A61M 25/0133; A61M 25/0105; A61M 25/0026;
(Continued)

(56) References Cited

U.S. PATENT DOCUMENTS 5,334,187 A 8/1994 Fischell et al.
5,531,687 A 7/1996 Snoke et al.
(Continued)

FOREIGN PATENT DOCUMENTS

EP 1998660 12/2008
WO WO 2015/063051 5/2015
WO WO 2015/063053 5/2015

*Primary Examiner* — Jason E Flick
(74) *Attorney, Agent, or Firm* — Brinks Gilson & Lione

(57) ABSTRACT

A steerable-catheter handle includes an outer housing with a multilumen catheter body extending generally distally therefrom. An internal track, including at least one track-defining lateral edge element, is disposed between distal and proximal terminal ends of the outer housing, which also houses a manifold engaged with the catheter body, a working-channel port member in fluid and mechanical communication with at least a first catheter lumen, a vacuum channel port member in fluid communication with at least one catheter lumen via one or both of the working channel port member and the manifold, and a generally proximal catheter port open to the internal track, where a distal endmost portion of the catheter mechanically communicates with one or more control surfaces so that the distal endmost portion of the catheter is deflectable along at least two intersecting axes, and where a portion of the catheter body extends removably through the internal track.

25 Claims, 9 Drawing Sheets

Related U.S. Application Data filed on Jul. 28, 2016, provisional application No. 62/367,938, filed on Jul. 28, 2016, provisional application No. 62/367,951, filed on Jul. 28, 2016, provisional application No. 62/367,959, filed on Jul. 28, 2016.

(51) Int. Cl.
*A61M 25/00* (2006.01)
*A61B 1/00* (2006.01)

(52) U.S. Cl.
CPC .... *A61M 25/0097* (2013.01); *A61M 25/0136* (2013.01); *A61M 25/0144* (2013.01); *A61M 25/09033* (2013.01); *A61B 1/00064* (2013.01); *A61M 25/0113* (2013.01); *A61M 25/0152* (2013.01); *A61M 2025/0079* (2013.01); *A61M 2025/0098* (2013.01); *A61M 2025/015* (2013.01); *A61M 2025/0161* (2013.01); *A61M 2025/0166* (2013.01); *A61M 2025/09125* (2013.01)

(58) Field of Classification Search
CPC .......... A61M 25/0113; A61M 25/0136; A61M 25/0147; A61M 2025/0079; A61M 2025/0098; A61M 2025/0161; A61M 2025/0166; A61M 2025/09125; A61M 25/0041; A61M 25/0097; A61M 25/0144; A61M 25/0152; A61M 25/09033; A61B 1/00064

USPC ..................................................... 604/95.04
See application file for complete search history.

(56) References Cited

U.S. PATENT DOCUMENTS

| | | |
|---|---|---|
| 6,146,355 A | 11/2000 | Biggs |
| 6,533,782 B2 | 3/2003 | Howell et al. |
| 7,198,599 B2 | 4/2007 | Goto et al. |
| 7,351,202 B2 | 4/2008 | Long |
| 7,371,211 B2 | 5/2008 | Akiba |
| 7,717,846 B2 | 5/2010 | Zirps et al. |
| 7,833,155 B2 | 11/2010 | Torii |
| 7,857,755 B2 | 12/2010 | Kupferschmid et al. |
| 7,922,650 B2 | 4/2011 | McWeeney et al. |
| 7,931,616 B2 | 4/2011 | Selkee |
| 8,096,943 B2 | 1/2012 | Melville |
| 8,257,344 B2 | 9/2012 | Ponzi et al. |
| 9,011,412 B2 | 4/2015 | Albritton, IV et al. |
| 9,101,736 B2 | 8/2015 | Qureshi |
| 9,302,073 B2 | 4/2016 | Bacher et al. |
| 2006/0252993 A1* | 11/2006 | Freed .................. A61B 1/0052 600/146 |
| 2007/0238928 A1 | 10/2007 | Maseda et al. |
| 2011/0184345 A1 | 7/2011 | Howell et al. |
| 2015/0057537 A1* | 2/2015 | Dillon ................. A61B 1/0014 600/431 |
| 2015/0073342 A1 | 3/2015 | Pacheco et al. |
| 2016/0089008 A1* | 3/2016 | Simmons .......... A61B 1/00128 600/106 |
| 2016/0262601 A1* | 9/2016 | Viebach .............. A61B 1/0125 |

\* cited by examiner

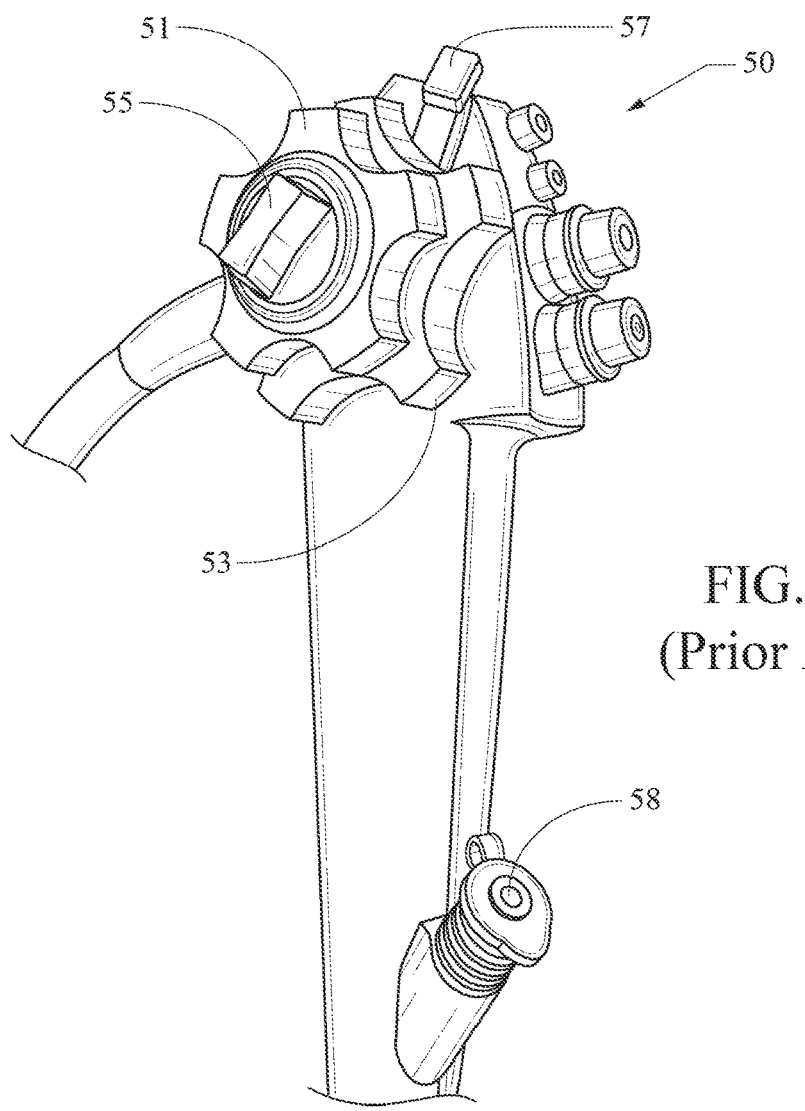
FIG. 1
(Prior Art)
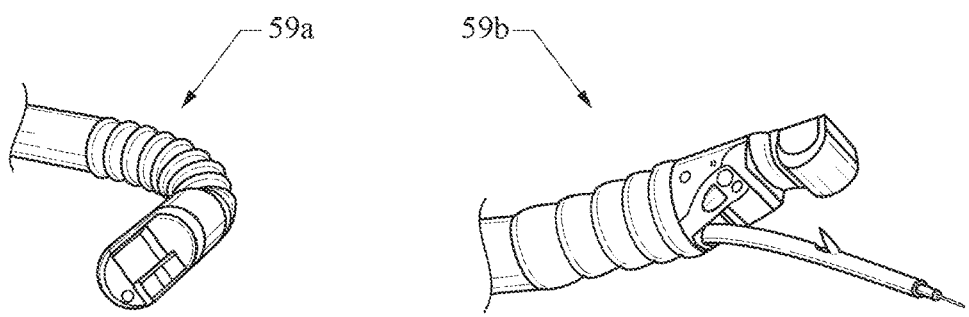
FIG. 1A
(Prior Art)
FIG. 1B
(Prior Art)

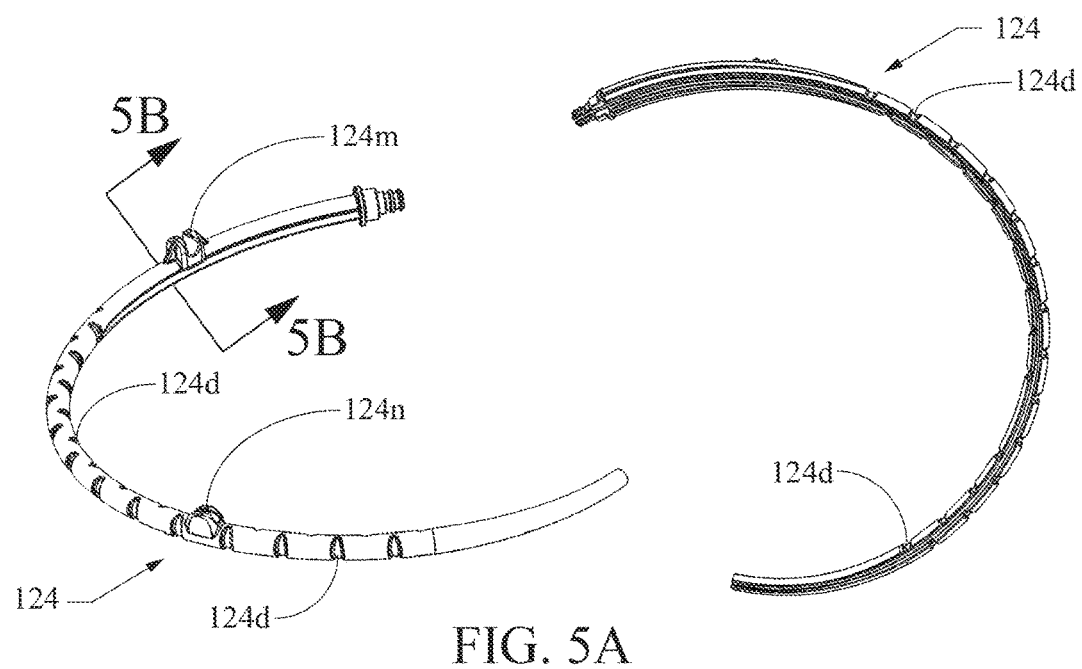
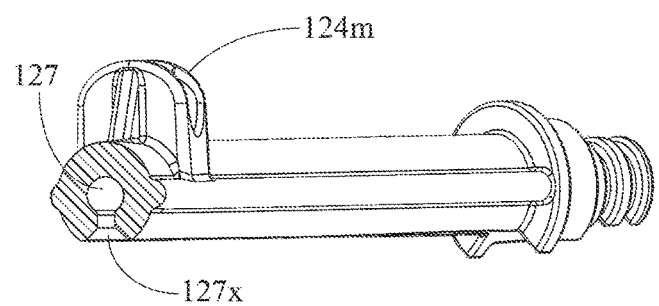
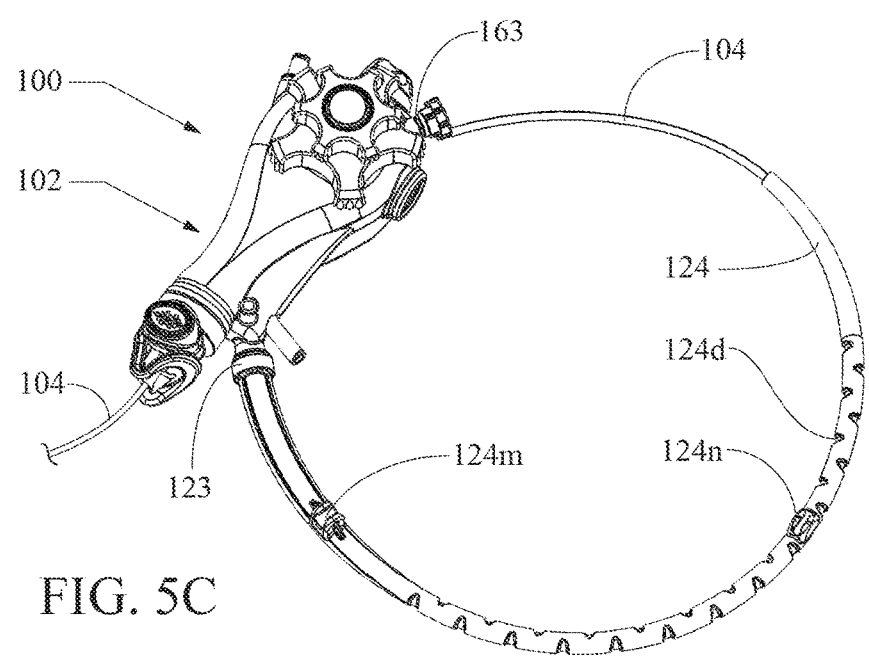

STEERABLE CATHETER HANDLE

CROSS-REFERENCE TO RELATED APPLICATIONS

This application is a non-provisional application which claims priority to U.S. provisional application Ser. Nos. 62/367,910; 62/367,918; 62/367,938; 62/367,951; and 62/367,959; all filed Jul. 28, 2016, each of which is incorporated by reference herein in its entirety.

TECHNICAL FIELD

Embodiments disclosed herein generally relate to steerable medical catheter devices, including endoscopes. More particularly embodiments disclosed herein relate to a structures and methods for a handle of a steerable small-diameter catheter.

BACKGROUND

Deflecting catheters, also referred to as steerable catheters are used in a variety of medical and non-medical procedures. In diagnostic and therapeutic medical procedures, a steerable catheter provides an operator (e.g., physician) with the ability to articulate the distal tip of the catheter in order to travel through constrained and/or tortuous anatomy, and/or to direct the distal catheter tip in a particular direction. Similar mechanisms are used in medical and nonmedical endoscopes to steer them to a target site and to orient a device portion (e.g., including a camera or other visualization means) in a desired direction.

In a typical design, control wires are manipulably attached at a proximal end of the device, and also attached at or near a distal end of the device. Such a configuration operates by manipulating one or more of the control wires to increase and/or decrease a generally longitudinal force on the distal device end that will deflect it in a desired direction. As described with reference to an existing steerable endoscopic camera device 50 of FIG. 1, the control wires may be actuated by rotation of control wheels 51, 53. Each control wheel can be rotated to operate a control wire or pair of control wires in a manner exerting push/pull tension on a deflectable distal device portion (not shown, but well-known in the art) to deflect that portion along a first plane, while the other control wheel operates similarly to deflect that portion along a second plane intersecting (e.g., orthogonal to) the first plane. At times, it is desirable to lock that distal device portion into a particular deflected orientation (e.g., so that the operator may execute another task requiring releasing hand contact with one or both control wheels). The illustrated device 50 includes a first brake for the first control wheel 51, with a twistable knob 55 for locking/unlocking an internal brake mechanism that operates along the central rotational axis of the first control wheel 51. The illustrated device 50 includes a second brake for the second control wheel 53, with a lever 57 for locking/unlocking an internal brake mechanism that operates by exerting a braking engagement along the central rotational axis of the second control wheel 53. One or both brake controls 55, 57 require a user to change his/her grip for actuation.

A variety of different steerable shaft constructions have been used in different prior catheters and endoscopes. Each shaft typically has at least one working channel that extends longitudinally therethrough (e.g., through a working channel port 58 in the handle, shown capped). A steerable catheter device may be configured as a gastrointestinal duodenoscope with a distal terminal end construction 59a as shown in FIG. 1A or as an endoscopic ultrasound (EUS) endoscope with a distal terminal end construction 59b as shown in FIG. 1B, which also shows a tool structure extending out through that scope's working channel lumen.

However, there are special challenges and needs for a small-diameter catheter (e.g., less than 10 mm, less than 5 mm, or less than 4 mm) configured for use through a side-viewing endoscope—such as a duodenoscope, potentially including designs like those shown in FIGS. 1-1B. In particular, such a device will need different resistance to crimping, kinking, and/or collapse along its length during operation and manipulation—including during introduction into and operation within a biliary tree of a human or non-human patient. Further, it is desirable for a handle of a steerable catheter device to attach directly and rigidly to a working port of a larger endoscope, for which reason it is desirable to have the handle to include physical features and functions that provide for management of fluid and vacuum, while also providing for operation of a camera, light element (s), steering along and between all four transverse axes relative to a catheter device shaft, and robust construction.

It is be desirable to provide a catheter shaft design that is configured and dimensioned for operation as a cholangioscope. Moreover, there is a need for a catheter device like this that provides economic diagnostic, therapeutic, and economic benefit to patients and caregivers by providing reliably predictable operative functionality and resistance to impaired structure or function during typical operations.

BRIEF SUMMARY

In one aspect, embodiments disclosed herein may include a handle for a steerable catheter device, including an endoscopy device such as a cholangioscope, as well as methods for making and/or using such a device.

In one aspect, embodiments disclosed herein may include steerable catheter handle including: an outer housing; a multilumen catheter body extending generally distally from the outer housing; a mounting mechanism at or near a distal terminal end of the outer housing; an internal track, disposed between the distal terminal end of the outer housing and a proximal terminal end of the outer housing, the internal track including at least one track-defining lateral edge element; a manifold engaged with the multilumen catheter body; a working channel port member extending outside an outer housing exterior surface and providing a path in fluid communication with at least a first lumen of the multilumen catheter; a vacuum channel port member in fluid communication with at least one lumen of the multilumen catheter via one or both of the working channel port member and the manifold; and a generally proximal catheter port open through an outer housing exterior surface and providing a path of mechanical communication with the internal track; where at least a distal endmost portion of the multilumen catheter is in mechanical communication with one or more control surfaces of the handle portion such that the distal endmost portion of the multilumen catheter is deflectable along at least two intersecting axes; and where a portion of the multilumen catheter body extends removably through the internal track.

BRIEF DESCRIPTION OF THE DRAWINGS

FIG. 1 is a view of a prior art steerable/deflectable catheter device embodied as an endoscope;

FIGS. 1A and 1B show distal terminal end configurations of prior art devices like that of FIG. 1, with and through which embodiments of the present device embodiments may be used;

FIGS. 5A-5B show a strain relief sleeve; and

FIG. 5C shows the device with the strain relief sleeve partially passed through by the catheter body, which is looped around through a central handle track.

DETAILED DESCRIPTION

Figure 2:
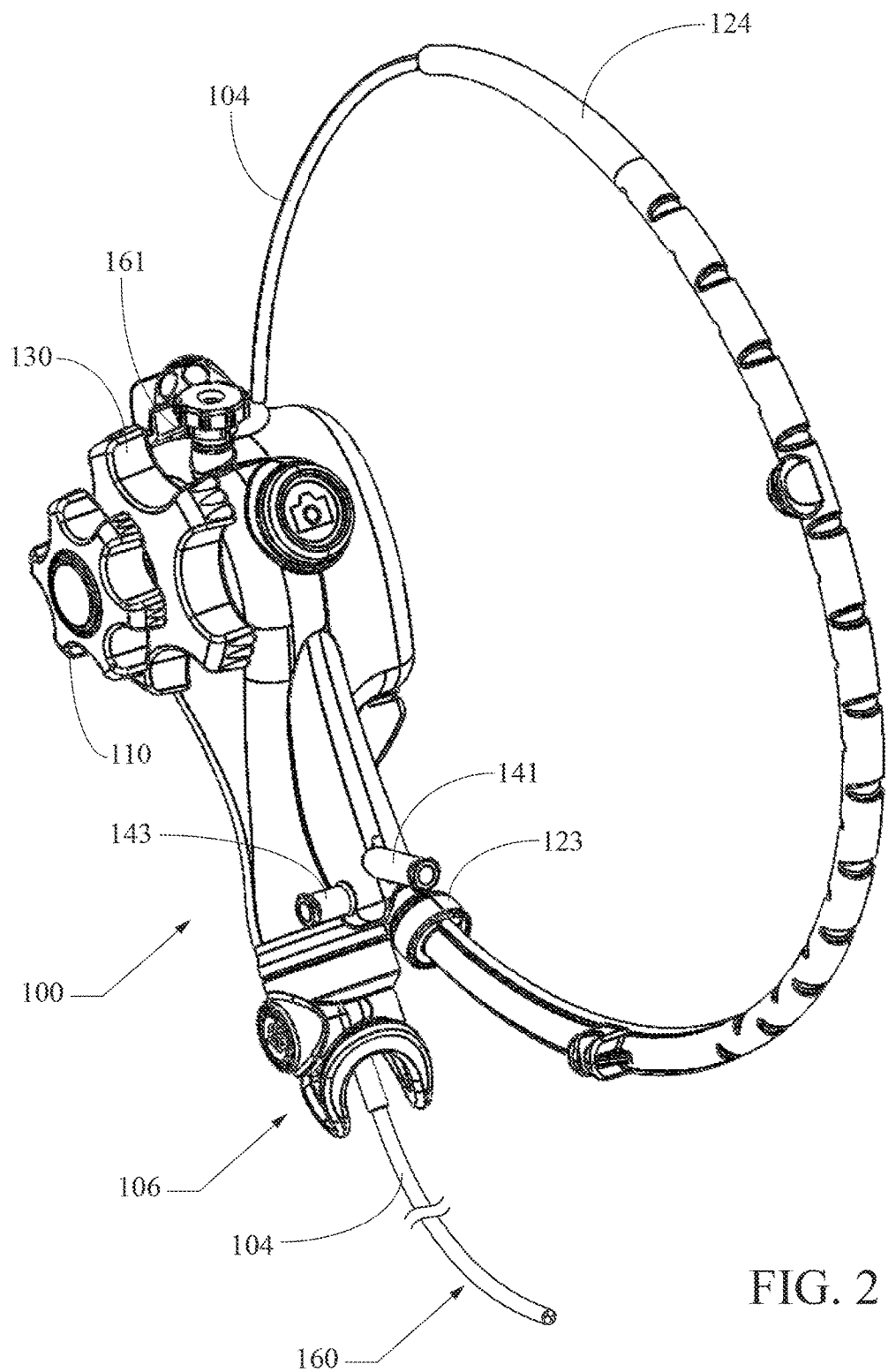
FIG. 2 depicts a perspective view of a steerable catheter device of the present disclosure.

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings may be but are not necessarily to scale, and in certain instances details may have been omitted that are not necessary for an understanding of embodiments disclosed herein, such as—for example—conventional fabrication and assembly.

Generally, the steerable catheter handle embodiments of the present disclosure provide structure for a small-diameter deflectable/steerable catheter (including one provided with visualization elements for use as an endoscope) to be attached to a larger "parent" scope, and with an internal manifold that provides structure for effective operation of the steerable shaft portion including manipulation and passage of fluids and/or devices.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. Reference herein to any industry standards (e.g., ASTM, ANSI, IEEE standards) is defined as complying with the currently published standards as of the original filing date of this disclosure concerning the units, measurements, and testing criteria communicated by those standards unless expressly otherwise defined herein.

The terms "proximal" and "distal" are used herein in the common usage sense where they refer respectively to a handle/doctor-end of a device or related object and a tool/patient-end of a device or related object. The terms "about," "substantially," "generally," and other terms of degree, when used with reference to any volume, dimension, proportion, or other quantitative or qualitative value, are intended to communicate a definite and identifiable value within the standard parameters that would be understood by one of skill in the art (equivalent to a medical device engineer with experience in this field), and should be interpreted to include at least any legal equivalents, minor but functionally-insignificant variants, standard manufacturing tolerances, and including at least mathematically significant figures (although not required to be as broad as the largest range thereof).

Embodiments of a handle are described with reference to FIGS. 2-4, where FIG. 2 shows a steerable catheter device of the present disclosure including a handle portion assembly 100 with a steerable catheter body 104 extending distally therefrom (which may have a default straight linear configuration, and for which is illustrated only a slightly-deflected distal end terminal lengthwise portion). Various embodiments may include one or more different steering control means known in the art. This illustrated embodiment includes a pair of control wheels, with an outer control wheel 110 and an inner control wheel 130. As set forth in greater detail below (including with reference to FIGS. 2A-2C), the outer control wheel 110 is disposed in mechanical communication with a pair of control wires that are operable, upon wheel rotation, to deflect at least the end portion 160 of the catheter body 104 along a first plane, and the inner control wheel 130 is disposed in mechanical communication with another pair of control wires that are operable, upon wheel rotation, to deflect the catheter body 104 along a second plane that may be generally orthogonal to the first plane, and is at least somewhat offset from that first plane. Simultaneous or sequential operation of the outer and inner wheels 110, 130 preferably will deflect the distal end portion 160 of the catheter body 104 in any direction around a 360-degree circle defined generally by a circumference of the catheter. The phrase "generally orthogonal" is used to refer to the objects being perpendicular, or very nearly so (for example, within 10° to 30°; in one embodiment, by way of non-limiting example, the planes may be offset by 112°/68° as shown in FIG. 4 with reference to the position and orientation of the parallel control wire lumens).

Steering mechanisms using control wires are well-known in the art including in U.S. Pat. Pub. No. 2015/0366435 to Williams, which is incorporated herein by reference in its entirety. The overall control structure described is also well known in the steerable device art, including particularly the endoscope art, but those devices lack the currently disclosed finely-controlled mechanism for efficient and effective tensioning of control wires. Certain embodiments in keeping with the present disclosure may include at least one visualization element (as well as supporting hardware and/or software, not shown—but well-known in the art and readily understandable as using electrical and/or optical devices such as CCD, fiber optic, CMOS, etc.) for use of such embodiments as endoscopic devices including, for example, as a cholangioscope configured for use with and through a larger endoscope. The illustrated handle embodiment 100 is configured for secure attachment to a working channel of a larger endoscope (e.g., as shown in FIG. 1), and it may include any number of different attachment/mounting mechanisms 106, such as—for example—those described and illustrated in U.S. Pat. App. Pub. No. 2015/0057537 and/or 2016/0089008, each of which is incorporated by reference herein in its entirety.

In FIG. 2, a strain-relief sheath 124 is shown attached to and extending from a near-distal catheter-base port 123 of the handle housing 102, which strain-relief sheath is described below in greater detail. A vacuum channel port member 141 and a flush port member 143 are also shown adjacent the near-distal catheter-base port 123 of the handle housing 102. A working channel port member 161 extends from a proximal end portion 161a of the handle housing 102 and provides for mechanical and fluid communication with at least one lumen of the catheter 104. As used herein, a path or structure providing "fluid communication" refers to a lumen or passage at least partially enclosed that is dimensioned and otherwise configured for movement therethrough of liquid and gas. As used herein, a path or structure providing "mechanical communication" refers to a lumen or passage at least partially enclosed that is dimensioned and otherwise configured for movement therethrough of a physical object (e.g., an endoscopic tool such as a needle, biopsy pincers, sphincterotome, needle-knife, guidewire, or other device).

Figure 2A:
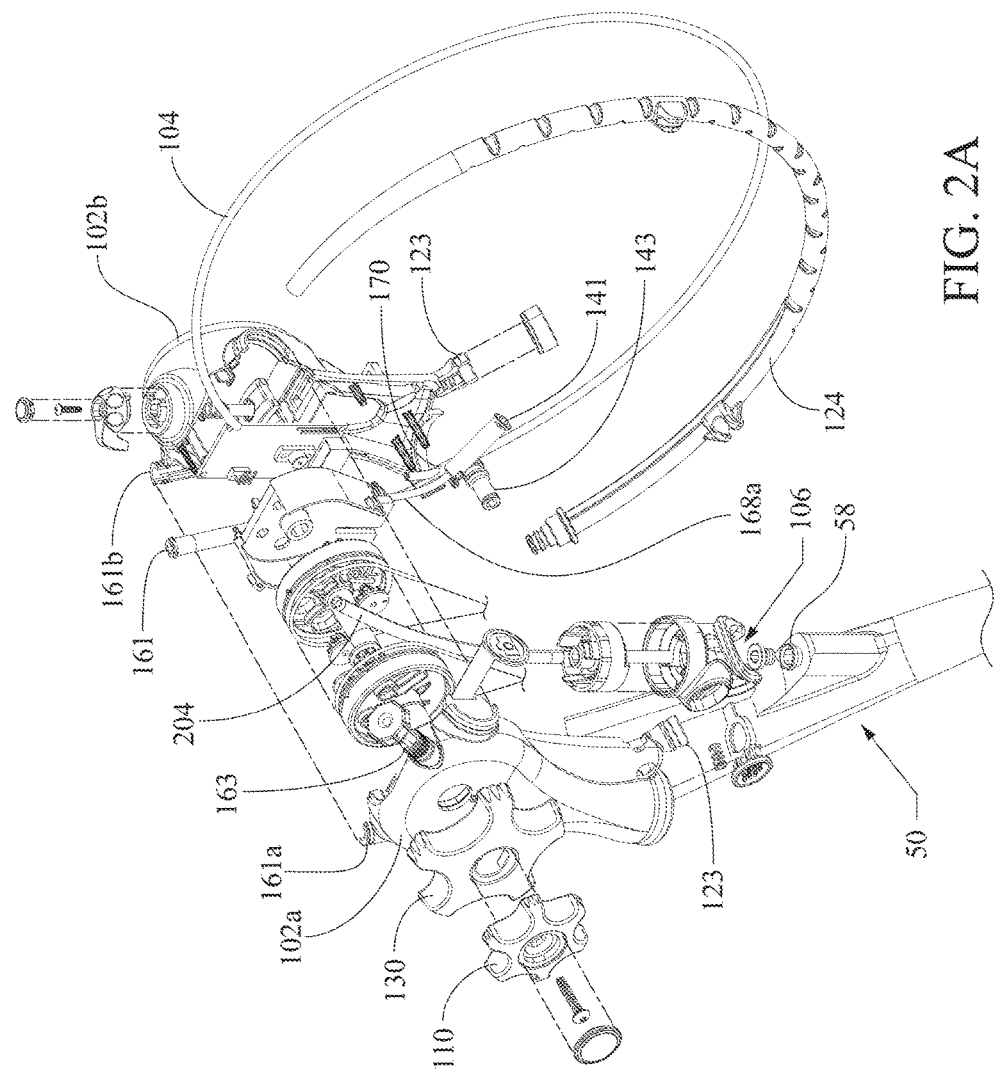
FIGS. 2A-2C show exploded views of the device of FIG. 2, depicting the arrangement of its components.
Figure 2B:
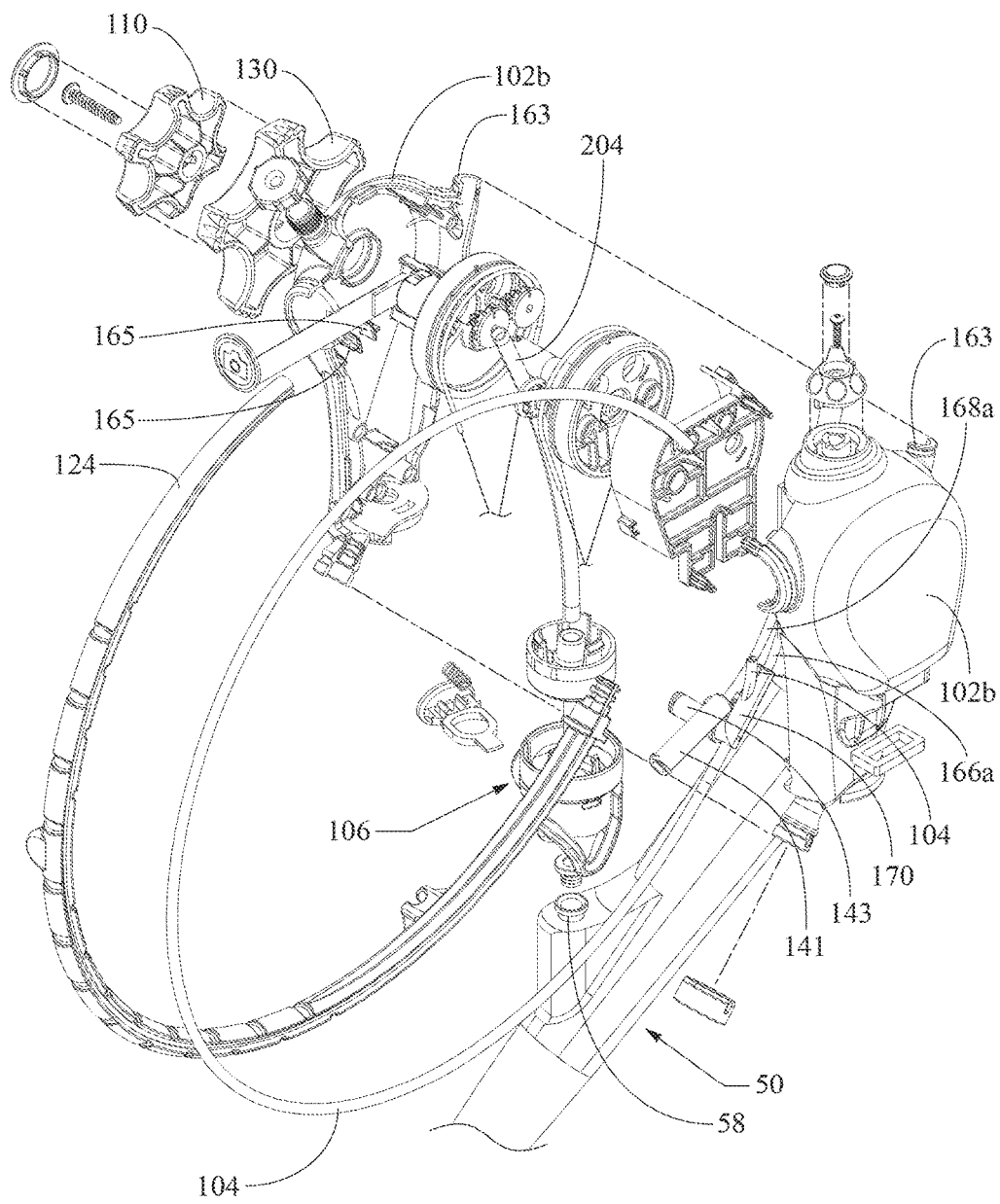
Figure 2C:
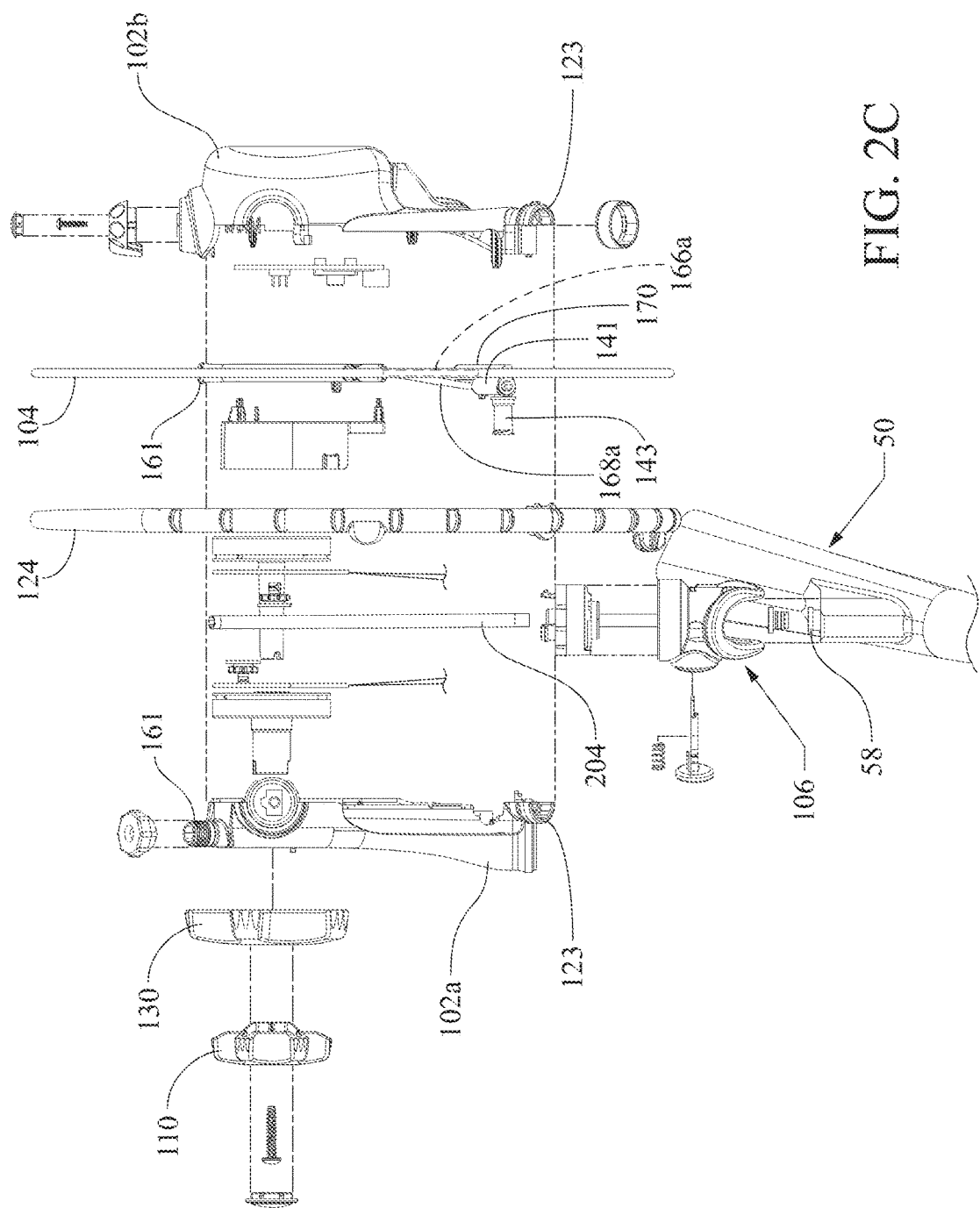

The exploded views of FIGS. 2A-2C show internal components and relative position/arrangement thereof, but certain components not being claimed in the present disclosure are not described in any detail. These views are shown positioned adjacent to a partially-illustrated larger steerable device such as an endoscope 50, where—as noted above—embodiments of the present device may be securely mounted thereto in a manner with the present catheter 104 extending into the working channel port 58. Most of the internal components are assembled between the first and second halves 102a, 102b of the handle housing 102. As shown in FIGS. 2 and 2A-2C, the multilumen catheter body 104 extends from a manifold 170 out through the near-distal catheter-base port 123 (through a strain relief sheath 124, if present) and loops around to re-enter a proximal catheter-track port 163 of the handle housing 102. The internal track is described below with reference to FIGS. 3A-3B.

The track does not need to be fully enclosed by other structures within the housing, but includes at least one track-defining lateral edge element 165, which helps define a track for the catheter body 104 to be removably directed from the proximal catheter-track port 163 through to an through a central opening of the distal mounting/attachment structure 106, through which that catheter body 104 may enter the working channel of a larger scope. In the exploded view of FIGS. 2A-2C, the track is provided with a track tube 204 configured to provide a closed, fluid-patent path of mechanical communication from the proximal catheter-track port 163 to the near-distal catheter-base port 123. The track tube 204 is also shown in FIG. 3B (in phantom line), with the catheter body extending through its longitudinal central lumen but is not shown in FIG. 3A. The track-defining lateral edge elements 165 do not need fully to enclose the track, but—as illustrated—serve to laterally stabilize the track tube 204 and hold it in alignment for a smooth transit of the catheter body 104 through a central longitudinal lumen of the track tube 204. As such, the portion of the multilumen catheter body 104 extending movably through the internal track can be removed entirely from the track while remaining attached to and extending generally distally from the outer housing 102. By "generally distally," it is meant that where the catheter is fixedly attached to the handle body, the catheter extends at a downward angle of less than 90° or less relative to the longitudinal axis from top to bottom of the handle body. Those of skill in the art, informed by the present disclosure, will appreciate that the internal mechanical/structural arrangement of the catheter, manifold, and communicating structures can be reversed (e.g., top-bottom) or otherwise oriented within a handle body, within the scope of the present disclosure.

In FIG. 3B, the working channel port member 161 and the manifold 170 are shown in longitudinal section (halfway through their lateral thicknesses). The working channel port member 161 includes a first longitudinal lumen 166 that provides fluid communication and mechanical communication (via the lumen of an intermediate first extension tube 166a and the manifold 170) with a working channel lumen 164 of the catheter body 104. Near the distal end of the working channel port member 161, a transverse channel 167 provides a path of fluid communication between a short second longitudinal lumen 168 and the first longitudinal lumen 166. An outside end terminus of the transverse channel 167 is shown as being sealed with a ball member 167a. The second longitudinal lumen 168 is in communication (via the lumen of an intermediate second extension tube 168a) with the vacuum channel port member 141. Each of the intermediate first extension tube 166a and the intermediate second extension tube 168a may be attached to the working channel port member 161 by that working channel port member 161 being overmolded around them to form a secure attachment with fluid-patent inner lumens.

This construction enables providing a vacuum to the working lumen 164 of the catheter 104, even when a diagnostic tool, therapeutic tool, or other device is attached to the working channel port member 161 and is occupying some or even most of the first longitudinal lumen 166 and the working lumen 164 of the catheter 104. During procedures, this provides for management of fluids (e.g., bodily fluids, flushing fluids) that can migrate up the working lumen 164. The orientation and position of the vacuum channel port member 141 keeps it out of the way for an operator who is manipulating the catheter 104, control wheels 110, 130, and other device features (see, e.g., FIG. 5C, which shows a vacuum line 141p with vacuum valve 141q extending from the vacuum channel port member 141).

Figure 3A:
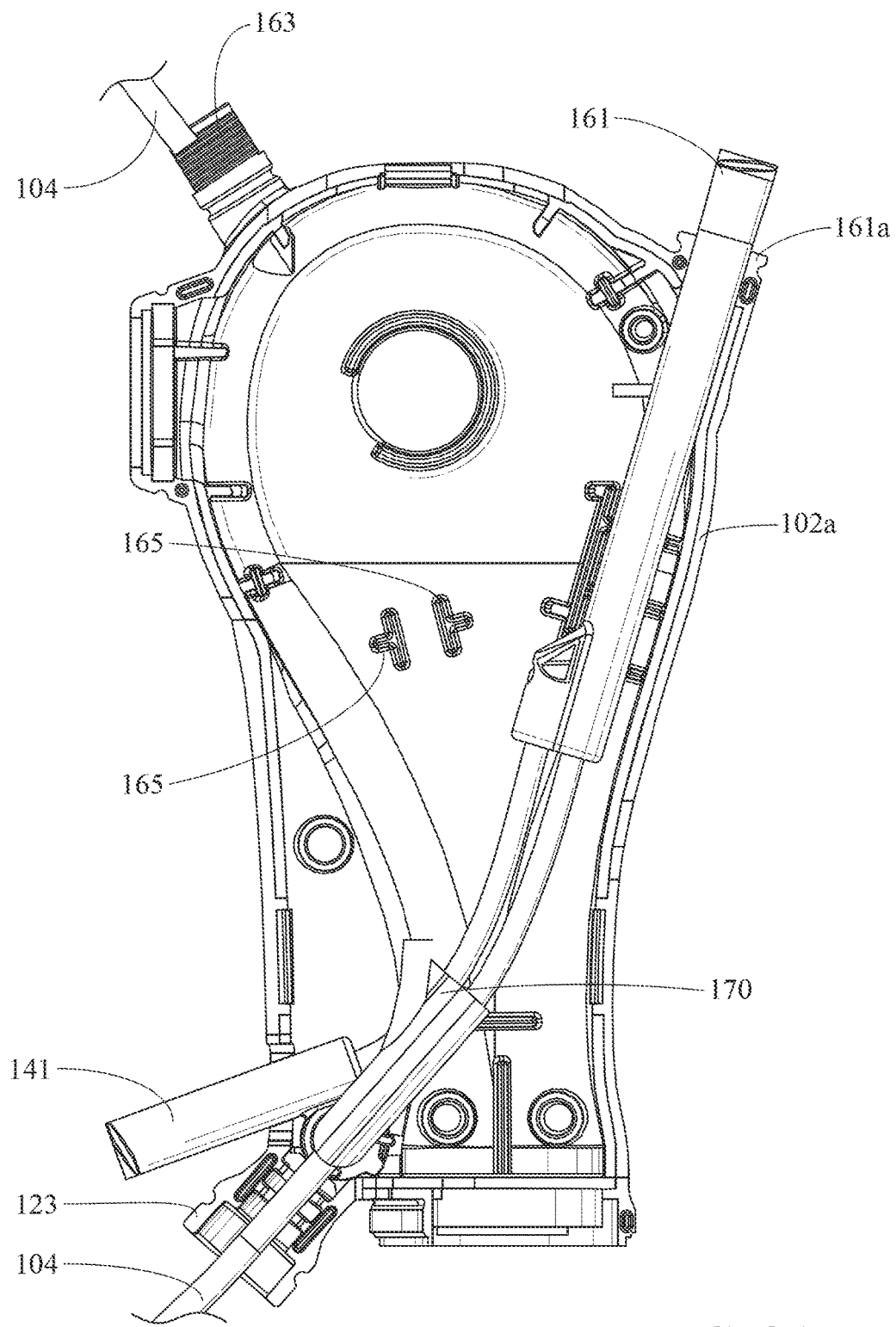
FIG. 3A is a partially disassembled view of a handle housing of the device of FIG. 2.
Figure 3B:
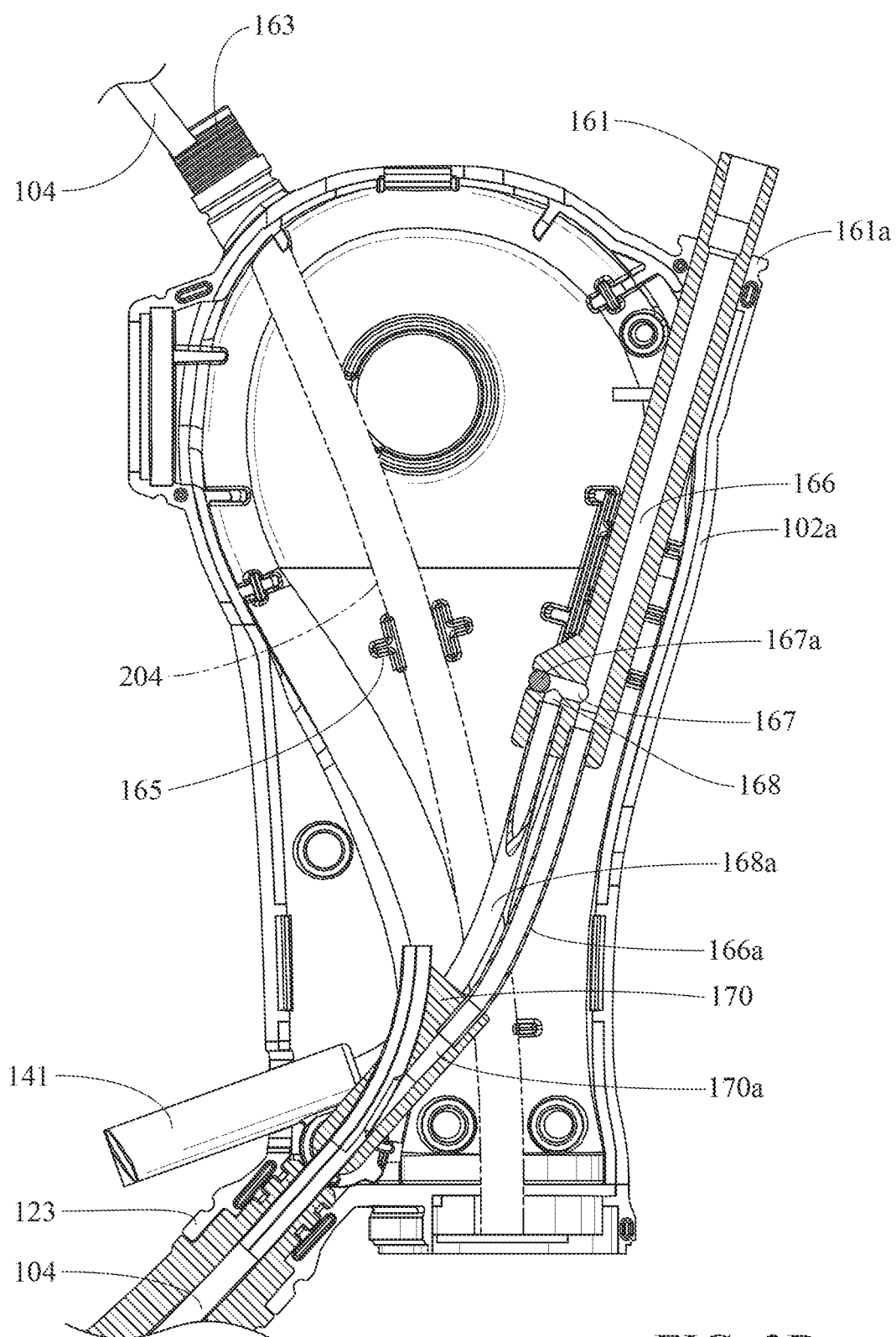
FIG. 3B shows the same structure and as FIG. 3A, but with a longitudinal section view taken along a plane that is half-way through the lateral thickness of the components shown in cross-section.
Figure 4:
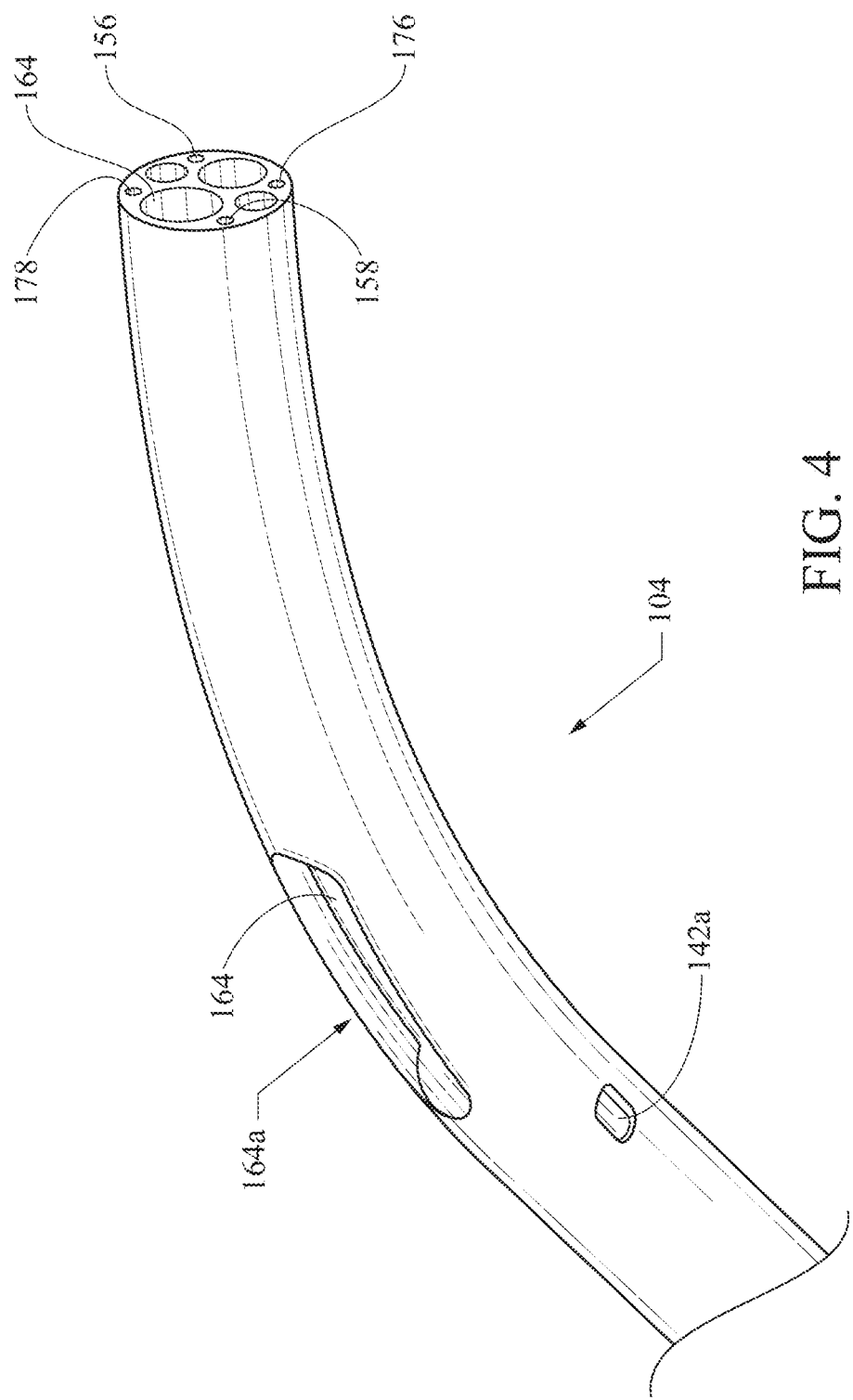
FIG. 4 shows a detail view of a portion of the catheter body from within handle housing.

The manifold 170 is shown in FIGS. 3A-3B, with reference also to FIGS. 2A-2C. As shown in FIG. 3B, with reference also to FIG. 4, a first longitudinal manifold lumen 170a is in fluid and mechanical communication (via the lumen of the intermediate first extension tube 166a) with the catheter working lumen 164. The first longitudinal manifold lumen 170a communicates with the catheter working lumen 164, as shown in FIGS. 3B and 4, via a skived opening 164a through the side wall of the catheter 104. A perspective view of the proximal terminal end of the catheter body 104 is shown in FIG. 4, including showing the catheter lumens: working lumen 164, control wire lumens 156, 158, 176, 178, and other channels that may be used, for example, for one or more of light source(s), camera or other visualization device, wire guide, vacuum, flushing, other accessories/tools, or other purposes and/or objects. The control wire lumens receive the control wires (shown with termination in FIGS. 2A-2C), and those wires provide mechanical communication between one or more control surfaces (e.g., wheels 110, 130) and the distal endmost portion 160 of the multilumen catheter body 104 so that the body will be deflectable along at least two intersecting axes.

As shown with reference to FIGS. 4 and 2A-2C, the flush port member 143 is illustrated as being disposed generally orthogonal to the longitudinal axis of the multilumen catheter body 104, to the manifold 170 with which the flush port member is attached, and to the manifold first lumen 170a. The flush port member 143 provides a path of fluid communication with at least one lumen of the multilumen catheter body 104 via a flush port skive 143a through the side wall of the catheter 104. The flush port skive 143a may open to the working lumen 164, but preferably is oriented radially about 90° from, and longitudinally near, the working lumen side skive 164a. In this position and orientation, the flush port skive 143a may open to a different lumen of the catheter body, which—in many embodiments will be a lumen other than the working lumen 164. As shown in the drawings, the multilumen catheter extends proximal of, through, and distal of the manifold, including extending out of the handle housing 102, then looping back around to extend movably and removably through its inner track and through the bottom distal terminal end of the handle housing. As shown in the drawings, the bottom/distal end of the manifold, from which the catheter 104 extends, is disposed at an acute angle relative to the bottom/distal end of a longitudinal axis of the handle body 102.

Each of the intermediate first extension tube 166a and the near-proximal end region of the catheter body 104 may be attached to/in the manifold 170 by the manifold being overmolded around them to form a secure attachment with fluid-patent inner lumens as described above. The flush port member 143 may be formed as a unitary part with the manifold 170, or as a separate member. In preferred embodiments, such as illustrated here, the common lumen extending through each of the working channel port member 161, intermediate first extension tube 166a, and manifold 170 provides a nearly straight/only slightly-curved path to minimize friction for tools being directed into and operated through the catheter working lumen 164 (with which that common lumen is continuous for both fluid and mechanical communication). When present, the strain relief sheath 124 helps to keep the catheter body 104 curvature out of, then back around into, the inner track of the handle body 102 at a larger radius, less-tightly-curved configuration (than the catheter without sheath) for the same reason, as minimizing friction will make operation of the steerable catheter and any tools used therethrough easier for operators and more mechanically efficient. Specifically, this configuration provides for reduced force of introduction of one or more tools through the catheter body lumen(s), and for reduced force required to operate those tools (e.g., needles, forceps, other diagnostic and/or therapeutic devices) when disposed to a target site via the catheter body—where the force is reduced as compared to other potential embodiments where the catheter body 104 would include and/or traverse tighter curves or bends.

The strain relief sheath 124 is described with further reference to FIGS. 5A-5C. In FIG. 5A is shown two opposite-side views of the strain relief sheath 124, and FIG. 5B shows a transverse section view thereof, taken along line 5B-5B of FIG. 5A. As shown in other drawing figures including at least FIG. 5C, the strain relief sheath 124 is configured to provide support for and around the length of the catheter body 104 that extends out from between the near-distal catheter-base port 123 and loops back around along an arc to the proximal catheter-track port 163. The strain relief sheath 124 preferably is made of a softer polymer than the proximal length of the catheter shaft, such as—for example—a Shore 78A polymer (where the proximal shaft length may be formed from a Shore 72 polymer or polymer blend). As shown in FIGS. 5A-5C, with particular reference to the section view of FIG. 5B, the strain relief sheath 124 includes a longitudinal lumen 127 extending through its entire length, and open along one lateral side via a slot 127x. The strain relief sheath lumen 127 has an inner diameter that preferably is about the same as, exactly the same as, or very slightly less than the outer diameter of the catheter shaft 104. The radial width of the strain relief sheath slot 127x is less than the outer diameter of the catheter shaft 104.

The strain relief sheath 124 is formed in a semicircular or other rounded form as illustrated (FIGS. 5A, 5C) to support the catheter 104 along the length already described and also resists kinking or crimping of any portion of the catheter body extending longitudinally through a longitudinal lumen of the strain relief sleeve. In particular, those of skill in the art will appreciate that actuation of the control wheels in a manner tensioning the control wires to steer/deflect the distal end of the catheter body requires transmitting force along those control wires. Because of the small diameter of the proximal catheter length 104, when subjected to such force, it would be prone to curving, buckling, or otherwise being distorted in a manner that would reduce the effective transmission of force from the handle to the distal catheter end. The strain relief sheath 124 provides radial support so that the force can more effectively be transmitted along the natural/default curved path (between the near-distal catheter-base port 123 and the proximal catheter-track port 163, described above) without distortion of the proximal catheter body portion, and minimal out-of-plane movement that would disperse the force transmission.

As shown in FIGS. 5A-5C, the strain relief sheath 124 may include semi-circumferential indented surfaces 124d along opposed sides. These indented surfaces 124d provide greater flexibility in the primary plane of the sheath body along which the catheter 104 curves, while simultaneously providing lesser flexibility for the sheath 124 to flex out of that primary plane. In the event that a greater length of the catheter body 104 needs to be advanced through the handle 102 than is allowed when fully engaged in the sheath 124, the sheath 124 can be peeled back with the catheter shaft 104 exiting through the slot 127x—for example from the distal sheath end as illustrated in FIG. 5C so that a distalmost length of the sheath 124 is no longer around the catheter body 104. In the embodiment illustrated, the strain relief sheath 124 may be constructed of a Santoprene™ polymer, about 45-47 cm in length (from the handle 102 to the distal end of the sheath 124), and curving within a circle of about 20-25 cm in diameter.

The indentations 124d may be configured as visible indicia of length at regular intervals. In certain embodiments, the strain relief sheath 124 may include at least one external friction clip member dimensioned for engaging an outer diameter portion of the multilumen deflectable catheter body, or another structure. The embodiment depicted herein, including in FIGS. 5A-5C, includes two clips. A proximal clip 124m includes a flexible/resilient pronged structure for clamping around a cord or cable. For example, in some embodiments an HDMI or other cable being used for data transmission (e.g., images) can be clipped into the proximal clip 124mm, or a cable or other columnar structure of a secondary device (not shown) being used with/through the overall device 100 (e.g., electrohydraulic lithotripsy cable) can be secured in the proximal clip 124m to help with device management and to relieve weight/stresses on a connection of that secondary device to the primary steerable catheter device 100. A distal clip 124n is also shown, which can be used to clip/hold a portion (e.g., distal or other length) of the catheter body—for example, during shipping, initial handling before introduction into/through a larger scope, or other use that will minimize the number of people needed in a suite for device management and that will make overall device handling more convenient for users.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

We claim:

1. A steerable catheter device, comprising:
   a handle portion including
      an outer housing;
      a multilumen catheter body extending generally distally from the outer housing;
      a mounting mechanism at or near a distal terminal end of the outer housing;
      an internal track, disposed between the distal terminal end of the outer housing and a proximal terminal end of the outer housing;
      a manifold engaged with the multilumen catheter body;
      a working channel port member extending outside an outer housing exterior surface and providing a path in fluid communication with at least a first lumen of the multilumen catheter;
   a vacuum channel port member in fluid communication with at least one lumen of the multilumen catheter via one or both of the working channel port member and the manifold; and
      a generally proximal catheter port open through an outer housing exterior surface and providing a path of mechanical communication with the internal track;
   where at least a distal endmost portion of the multilumen catheter is in mechanical communication with one or more control surfaces of the handle portion such that the distal endmost portion of the multilumen catheter is deflectable along at least two intersecting axes; and
   where a portion of the multilumen catheter body extends removably through the internal track.

2. The steerable catheter device of claim 1, where the portion of the multilumen catheter body extending movably through the internal track can be removed entirely from the internal track while remaining attached to and extending generally distally from the outer housing.

3. The steerable catheter device of claim 1, where the path of fluid communication between the working channel port member and the at least a first lumen of the multilumen catheter is provided via a working channel lumen of the manifold open through a catheter side wall skive into the at least one lumen of the multilumen catheter.

4. The steerable catheter device of claim 3, where the vacuum channel port fluid communication with at least one lumen of the multilumen catheter is provided via a vacuum lumen in the working channel port member, which vacuum lumen is disposed in fluid communication with the at least a first lumen of the multilumen catheter.

5. The steerable catheter device of claim 4, where the vacuum lumen is disposed in fluid communication with the at least a first lumen of the multilumen catheter via a transverse channel between the vacuum lumen in the working channel port member and a primary longitudinal working channel lumen.

6. The steerable catheter device of claim 3, further comprising a flush channel in fluid communication, via the manifold, with at least one lumen of the multilumen catheter.

7. The steerable catheter device of claim 6, where the flush channel is disposed generally orthogonal to a passage within the manifold through which the multilumen catheter is disposed.

8. The steerable catheter device of claim 1, where the internal track defines a path of mechanical communication between
   a central opening through the mounting mechanism and the generally proximal catheter port.

9. The steerable catheter device of claim 1, where the internal track further includes an enclosed tubular space through which the multilumen catheter is movable.

10. The steerable catheter device of claim 1, further comprising a strain relief sleeve disposed immediately adjacent and in mechanical communication with a distal end opening of the internal track, where the strain relief sleeve includes durometer that resists kinking or crimping of a catheter body passed through a strain relief sleeve lumen extending longitudinally through the strain relief sleeve.

11. The steerable catheter device of claim 10, where the strain relief sleeve includes a splittable lengthwise portion with a split or weakened wall that can be split and moved away from encompassing a catheter passing through the strain relief sleeve lumen.

12. The steerable catheter device of claim 1, where the manifold includes a first passage that
   coaxially receives a first extension tube extending from the working channel port member, and
   provides the path in fluid communication with the at least a first lumen of the multilumen catheter.

13. The steerable catheter device of claim 1, where the multilumen catheter extends proximal of, through, and distal of the manifold.

14. The steerable catheter device of claim 1, where the internal track includes a track tube member defining a tubular passage.

15. A handle assembly for a steerable catheter, the handle assembly comprising:
   a proximal end and a distal end;
   a proximal working channel port member including a first longitudinal lumen, a second longitudinal lumen shorter than the first, and a transverse channel providing fluid communication between the first and second longitudinal lumens;
   a vacuum port member including a longitudinal vacuum lumen disposed in fluid communication with the second longitudinal lumen;
   a distal manifold member including a manifold working lumen disposed in fluid communication with the first longitudinal lumen; and
   an internal track disposed generally longitudinally between the proximal end and the distal end, at least partially next to the manifold, where the internal track provides for passage next to the manifold of a multilumen deflectable catheter body, which multilumen deflectable catheter body extends distally externally from the manifold, loops around to, and through, the proximal end, and extends removably through the internal track.

16. The handle assembly of claim 15, where the internal track includes a track tube member defining a tubular passage through which the multilumen deflectable catheter body removably extends.

17. The handle assembly of claim 15, where the manifold includes a first passage that
coaxially receives a first extension tube extending from the working channel port member, and
provides the path in fluid communication with the at least a first lumen of the multilumen catheter.

18. The handle assembly of claim 15, where the multilumen catheter extends proximal of, through, and distal of the manifold.

19. The handle assembly of claim 18, where at least one lumen of the multilumen catheter is in fluid communication and mechanical communication with the first longitudinal lumen of the proximal working channel port member.

20. The handle assembly of claim 15, further comprising a strain relief sleeve disposed immediately adjacent of and including a longitudinal sleeve lumen in mechanical communication with the internal track, where the strain relief sleeve includes durometer that resists kinking or crimping of any portion of the catheter body extending longitudinally through a longitudinal lumen of the strain relief sleeve.

21. The handle assembly of claim 20, where the strain relief sleeve includes an open slit along at least a longitudinal portion of the longitudinal lumen of the strain relief sleeve, and where the durometer of the sleeve provides sufficient flexibility to allow the multilumen deflectable catheter body to be passed non-destructively through the open slit, where a width of slit is less than an outer diameter of the multilumen deflectable catheter body.

22. The handle assembly of claim 20, where the strain relief sleeve includes visible indicia of length at regular intervals, at least one external friction clip member dimensioned for engaging an outer diameter portion of the multilumen deflectable catheter body, or both.

23. The handle assembly of claim 20, where the strain relief sleeve includes a length that extends from adjacent the manifold around an arc to the proximal end of the internal track.

24. The handle of claim 23, where the arc of the strain relief sleeve provides a path longitudinally through the longitudinal lumen of the strain relief sleeve that, when the path is occupied by a multilumen deflectable catheter body length, said multilumen deflectable catheter body length is prevented from kinking, crimping, or both.

25. The handle of claim 15, where a distal length end of the manifold is disposed at an acute angle relative to a bottom distal longitudinal end of the handle assembly.

* * * * *